United States Patent
Kwon et al.

(10) Patent No.: US 11,433,002 B2
(45) Date of Patent: Sep. 6, 2022

(54) DENTAL LINER AND MANUFACTURING METHOD THEREFOR

(71) Applicant: KYUNGPOOK NATIONAL UNIVERSITY INDUSTRY-ACADEMIC COOPERATION FOUNDATION, Daegu (KR)

(72) Inventors: Tae Yub Kwon, Daegu (KR); Hee Sung Lee, Ulsan (KR); An Na Seo, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 407 days.

(21) Appl. No.: 16/639,519

(22) PCT Filed: Aug. 8, 2018

(86) PCT No.: PCT/KR2018/009015
§ 371 (c)(1),
(2) Date: Feb. 14, 2020

(87) PCT Pub. No.: WO2019/035593
PCT Pub. Date: Feb. 21, 2019

(65) Prior Publication Data
US 2021/0137794 A1 May 13, 2021

(30) Foreign Application Priority Data

Aug. 18, 2017 (KR) .................. 10-2017-0104699

(51) Int. Cl.
| | | |
|---|---|---|
| *A61K 6/40* | (2020.01) | |
| *A61K 6/70* | (2020.01) | |
| *A61K 6/20* | (2020.01) | |
| *A61K 6/60* | (2020.01) | |
| *A61K 6/818* | (2020.01) | |

(52) U.S. Cl.
CPC .................. *A61K 6/40* (2020.01); *A61K 6/20* (2020.01); *A61K 6/60* (2020.01); *A61K 6/70* (2020.01); *A61K 6/818* (2020.01)

(58) Field of Classification Search
CPC ........ A61K 6/30; A61C 13/00; A61C 13/083; A61Q 11/00
USPC .......................................... 424/600
IPC .................... A61Q 11/00; A61K 6/30
See application file for complete search history.

(56) References Cited

U.S. PATENT DOCUMENTS

| | | | |
|---|---|---|---|
| 8,957,126 B2 | 2/2015 | Rusin et al. | |
| 9,517,186 B2 | 12/2016 | Rusin et al. | |
| 10,125,054 B2 | 11/2018 | Lee et al. | |
| 2009/0215010 A1 | 8/2009 | Tagami et al. | |
| 2014/0367613 A1 | 12/2014 | Mashio et al. | |

FOREIGN PATENT DOCUMENTS

| | | |
|---|---|---|
| JP | 2006212065 A | 8/2006 |
| KR | 20070086324 A | 8/2007 |
| KR | 20140108275 A | 9/2014 |
| KR | 101627083 B1 | 6/2016 |
| KR | 20160112880 A | 9/2016 |
| WO | 2008/023775 A1 | 2/2008 |
| WO | 2016/124758 A1 | 8/2016 |
| WO | 2016/188914 A1 | 12/2016 |
| WO | 2019/035593 A1 | 2/2019 |

OTHER PUBLICATIONS

Japanese Decision to Grant Patent for JP Application No. 2020-508547 filed on behalf of Kyungpook National University dated Mar. 23, 2021 5 pages (English + Original).
International Search Report for International Application No. PCT/KR2018/009015 filed on Aug. 8, 2018 on behalf of Kyungpook National University dated Oct. 4, 2018 5 pages (English + Original).
Jung H.K. et al. "The Effect of Zirconia Powder Applications on the Shear Bond Strength between Zirconia and Feldspar Ceramic" *Korean Journal of Dental Materiais*, Dec. 2014, vol. 4, pp. 291-295 (English Abstract + Original).
Korean Decision to Grant a Patent for Korean Application No. 1020170104699 filed on Aug. 18, 2017 on behalf of Kyungpook National University dated Mar. 26, 2019 7 pages (Partial English + Original).
Korean Notice of Preliminary Rejection for Korean Application No. 1020170104699 filed on Aug. 18, 2017 on behalf of Kyungpook National University dated Jan. 2, 2019 8 pages (Partial English + Original).
Lee H.S. et al., "The Application of a Novel Ceramic Liner containing Zirconia Improves Bonding between Zirconia and Veneering Porcelain" *Materials*, 2017, 11 pages.
Written Opinion for International Application No. PCT/KR2018/009015 filed on August 8. 2018 on behalf of Kyungpook National University dated Oct. 4, 2018 8 pages (English + Original).

*Primary Examiner* — Walter E Webb
(74) *Attorney, Agent, or Firm* — Steinfl + Bruno LLP

(57) ABSTRACT

A dental liner and a manufacturing method therefor are disclosed. The dental liner is a dental liner for coupling feldspar porcelain and zirconia and includes: silicon dioxide; aluminum oxide; 1,4-butanediol for maintaining the moisture of the dental liner and preventing the generation of layers; and a zirconia powder for coupling the dental liner and zirconia by strengthening chemical bonding of the dental liner and zirconia.

6 Claims, 9 Drawing Sheets

DENTAL LINER AND MANUFACTURING METHOD THEREFOR

CROSS REFERENCE TO RELATED APPLICATIONS

The present application is the U.S. national stage of International Patent Application PCT/KR2018/009015 filed internationally on Aug. 8, 2018, which, in turn, claims priority to Korean Patent Application No. 10-2017-0104699 filed on Aug. 18, 2017.

TECHNICAL FIELD

The present invention relates to a dental liner and a method of manufacturing the same. More particularly, the present invention relates to a dental liner for bonding feldspar porcelain and zirconia and a method of manufacturing the same.

BACKGROUND ART

Recently, zirconia ceramic has been used as a restoration material for esthetic dentistry. However, since an all-ceramic crown having a single structure in which zirconia is used is hard to be used, generally a restoration in which a surface of zirconia is veneered with feldspar porcelain is used.

As a method of veneering a surface of zirconia with feldspar porcelain, there are a method of bonding feldspar porcelain to a surface of zirconia which has been roughened by using a sand blasting treatment on the surface of zirconia, a method of bonding feldspar porcelain and zirconia by using a liner to enhance chemical bonding force between feldspar porcelain and zirconia, a method of veneering a surface of zirconia with feldspar porcelain without any treatment, and the like.

A method of bonding feldspar porcelain to a surface of zirconia which has been roughened by using a sand blasting treatment may produce cracks on the surface of zirconia. Therefore, since a method of using a sand blasting treatment raises a fracture risk, it is a rarely used method.

A method of using a liner to enhance chemical bonding force between feldspar porcelain and zirconia is hardly used. The reason is that the binding force between feldspar porcelain and the liner is high, but the binding force between the liner and zirconia is low, and thus, the chemical bonding force between feldspar porcelain and zirconia is not enhanced. Accordingly, a method of veneering a surface of zirconia with feldspar porcelain without any treatment is generally used.

However, when a surface of zirconia is veneered with feldspar porcelain without any treatment, a probability that fracture occurs in the interface or the inside of the restoration formed, is increased.

In addition, though a fluorescent material is added to the veneered feldspar porcelain, it is more preferred to impart a fluorescent effect to the inside of the feldspar porcelain for reproducing a fluorescent effect which is similar to a natural tooth. To this end, it is the most aesthetic to impart fluorescence to the interface between the feldspar porcelain and zirconia.

Accordingly, there is a need for technology to increase binding force between zirconia and feldspar porcelain simultaneously with solving the aesthetic problem.

Technical Problem

The present invention provides a dental liner which increases chemical bonding force between feldspar porcelain and zirconia to allow feldspar porcelain to be bonded to zirconia without a fracture risk and reproduce a color tone having the same structure as a natural tooth to impart aesthetics.

Technical Solution

According to an aspect of the present invention, a dental liner for bonding feldspar porcelain and zirconia includes silicon dioxide; aluminum oxide; 1,4-butanediol for retaining moisture of the dental liner and preventing occurrence of layers; and zirconia powder for enhancing chemical bonding between the dental liner and the zirconia to bond the dental liner and the zirconia.

When the dental liner is bonded to the zirconia and then fired, the dental liner may further include cryolite for melting the dental liner at a temperature in a predetermined range.

The predetermined temperature range may be 900° C. to 1000° C.

The dental liner may further include bismuth oxide for imparting fluorescence to the zirconia, and the bismuth oxide may be dissolved in hydrochloric acid or nitric acid.

According to another aspect of the present invention, a method of manufacturing a dental liner for bonding feldspar porcelain and zirconia includes: mixing silicon dioxide, aluminum oxide, zirconia powder, and cryolite; adding 1,4-butanediol for retaining moisture of the dental liner and preventing occurrence of layers and performing mixing; and dissolving bismuth oxide for imparting fluorescence to the zirconia in hydrochloric acid or nitric acid and then mixing the bismuth oxide dissolved in hydrochloric acid or nitric acid.

The dental liner may include 50 to 60 parts by weight of the silicon dioxide; 5 to 10 parts by weight of the aluminum oxide; 10 to 20 parts by weight of the zirconia powder; 5 to 10 parts by weight of the cryolite; 20 to 30 parts by weight of the 1,4-butanediol; 1 to 5 parts by weight of the bismuth oxide; and 1 to 5 parts by weight of the hydrochloric acid or nitric acid.

Advantageous Effects

According to the exemplary embodiments of the present invention as described above, a dental liner including 1,4-butanediol, zirconia powder, and cryolite may be used to increase chemical bonding force between zirconia and feldspar porcelain and decrease a fracture risk.

In addition, a dental liner including bismuth oxide may be used to reproduce a color tone identical to that of a natural tooth in zirconia veneered with feldspar porcelain, thereby maintaining aesthetics.

The effects of the present invention are not limited by the effects mentioned above, and other effects which have not been mentioned may be clearly understood by an ordinary person skilled in the art from the following description.

BEST MODE FOR CARRYING OUT THE INVENTION

Figure 1A:
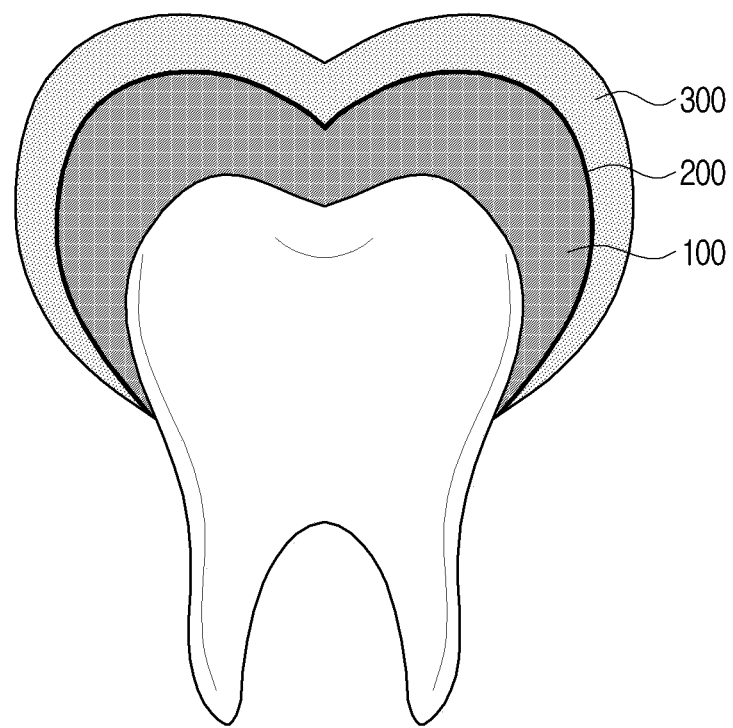
FIGS. 1A and 1B are block diagrams showing a bonding relationship of zirconia, a liner, and a feldspar porcelain according to an exemplary embodiment of the present invention.

Hereinafter, exemplary embodiments of the present invention will be described in detail with reference to the accompanying drawings. Advantages and features of the present invention and methods to achieve them will be apparent from reference of exemplary embodiments described below in detail together with the accompanying drawings. However the present invention is not limited to exemplary embodiments disclosed later, but will be implemented in various forms, and the exemplary embodiments are provided so that the disclosure of the present invention is complete and those skilled in the art to which the present invention pertains can easily understand the scope of the present invention, and thus, the present invention will be only defined by the scope of the appended claims. Like reference numerals throughout the description denote like elements.

Unless otherwise defined herein, all terms used herein (including technical and scientific terms) may have the meaning that is commonly understood by those skilled in the art. In addition, the terms defined in a commonly used dictionary are not ideally or excessively interpreted, unless otherwise clearly or particularly defined.

Figure 1B:
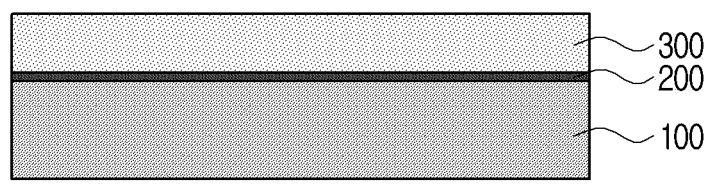

FIG. 1A is a block diagram illustrating that zirconia 100, a liner 200, and feldspar porcelain 300 are bonded to a tooth according to the present invention, and FIG. 1B is a cross-sectional diagram illustrating that zirconia 100, a liner 200, and a feldspar porcelain 300 are bonded according to the present invention.

Referring to FIG. 1A, a tooth is covered with zirconia 100, a surface of the zirconia 100 is coated with a liner 200, and the coated liner 200 is veneered with feldspar porcelain 300. Veneering means thin covering.

In addition, referring to FIG. 1B, the liner 200 for bonding the zirconia 100 and the feldspar porcelain 300 is in a paste state and has the smallest thickness, and the thickness of zirconia 100 is the largest. The thickness of the feldspar porcelain 300 is smaller than zirconia 100 and larger than the liner 200. The reason why zirconia 100 is thicker than the feldspar porcelain 300 will be described later in FIG. 2.

Zirconium (Zr) which is a metal belonging to Group 4 of the periodic table is an off-white hard transition metal having gloss and similar to titanium. However, zirconium has better biocompatibility than titanium. Therefore, zirconium may be used as a structure of an implant instead of titanium. In addition, zirconium is mainly produced as zicon and has strong resistance to corrosion.

Zirconia 100 is another name of zirconium oxide (IV) ($ZrO_2$). A molecular weight of zirconia is 123.22, and a melting point thereof is about 2715° C. Zirconia has a high refractive index and a high melting point, thereby having high corrosion resistance. Corrosion resistance refers to a property of a metal surface which is easy to be deteriorated by oxidation and sulfuration in a gas phase or liquid phase.

When pure zirconia is subjected to firing at a high temperature and cooled to room temperature, a crystal structure is phase-transited from a tetragonal phase to a monoclinic phase. When phase-transited, a volume of pure zirconia expands by about 3 to 5%. Cracks are produced inside expanded pure zirconia and the strength of a material is decreased.

As an industrial material, stabilized zirconia is generally used. When about 3 to 5% of calcium oxide (CaO), cerium oxide ($CeO_2$), magnesium oxide (MgO), yttrium oxide ($Y_2O_3$), and the like are added to pure zirconia, a tetragonal zirconia polycrystal TZP is formed. A compound such as calcium oxide (CaO), cerium oxide ($CeO_2$), magnesium oxide (MgO), and yttrium oxide ($Y_2O_3$) is also referred to as a "stabilizer". The tetragonal zirconia polycrystal to which a stabilizer is added may maintain a tetragonal phase at room temperature as well as at a high temperature.

In particular, most of the zirconia used as a dental material is an yttria-tetragonal zirconia polycrystal (Y-TZP) to which 3 mol % of yttria is added. In the present invention also, zirconia 100 may refer to an yttria-tetragonal zirconia polycrystal (Y-TZP).

A crown refers to an artificial crown, and is generally used for preventing fracture of an endodontic-treated tooth. When a tooth falls out or is damaged, a bridge treatment which is one of prosthetic treatments may be used. A bridge treatment is a treatment in which a prosthesis of a damaged tooth is fabricated and also prothesises of teeth positioned at both sides of the damaged tooth are fabricated, and the teeth are covered with the fabricated prothesises. Here, zirconia 100 may be used as an aesthetic material instead of porcelain-fused-to-metal (PFM) which is used as a bridge prothesis. PFM refers to a porcelain fused metal crown. A porcelain fused metal crown refers to a ceramic crown of which the inside is made of metal and the outside is made of ceramic. In addition, zirconia 100 may be used even in a stressful part or in the case of having a metal allergy.

Zirconia 100 has a flexural strength of 800 to 1,500 MPa and may have a structure having high resistance to fracture.

Zirconia 100 may be manufactured in a desired form of a prosthesis by mechanical cutting using a computer-assisted design/computer assisted manufacturing (CAD/CAM) method. However, zirconia 100 which is inappropriate for being used as a single one body crown is more translucent than a metal alloy, but is essentially white and opaque.

Feldspar porcelain 300 may contain 75 to 85% of feldspar which lowers the melting point to act as a binder, 12 to 22% of silicon dioxide which acts as a skeleton of porcelain, and 3 to 5% of clay which imparts plasticity.

An opaquer may be used in the feldspar porcelain 300 so that a dark side is not shown during dental laboratory working.

When the feldspar porcelain is bonded to prepared tooth enamel, a tooth bonded to feldspar porcelain may be retained for 20 to 25 years due to compression strength produced in the feldspar porcelain 300. Preparation refers to teeth trimming. However, the fracture strength of the feldspar porcelain 300 itself is about 70 to 110 MPa, which is relatively low. Feldspar porcelain 300 having relatively low fracture strength and zirconia 100 having relatively high fracture strength but having a different color tone from that of a natural tooth have low binding force to each other. Therefore, the liner 200 is used for veneering the surface of zirconia 100 with feldspar porcelain 300.

Figure 2:
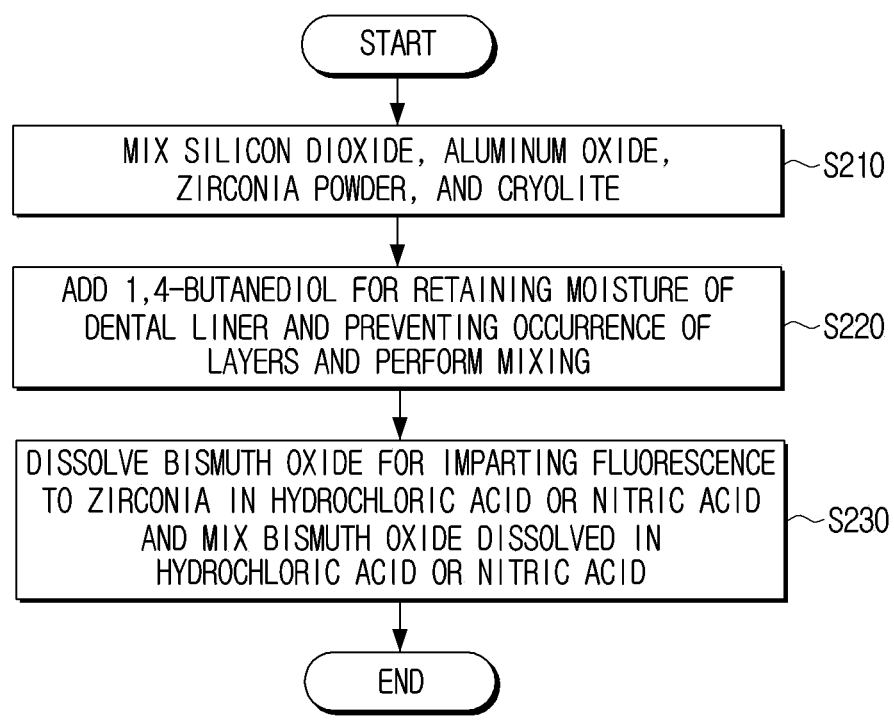
FIG. 2 is a flow chart showing a method of manufacturing a dental liner according to an exemplary embodiment of the present invention.

FIG. 2 is a flow chart describing a method of manufacturing a dental liner according to an exemplary embodiment of the present invention. Hereinafter, a method of manufacturing a dental liner of the present invention will be described, referring to FIG. 2.

Referring to FIG. 2, as a method of manufacturing a dental liner for bonding feldspar porcelain and zirconia, silicon dioxide, aluminum oxide, zirconia powder, and cryolite are mixed (S210).

Though silicon dioxide and aluminum oxide are included in the conventional liner components, a main component of a common liner is silicon dioxide. Since feldspar porcelain also includes the silicon dioxide component, the mechanical properties of the liner are similar to the mechanical properties of feldspar porcelain. Therefore, the binding force between the liner and feldspar porcelain is high.

However, a main component of zirconia is zirconium, and zirconium and silicon dioxide which is the main component of the liner have different chemical properties from each other. Therefore, the binding force between the liner and zirconia is lower than the binding force between feldspar porcelain and zirconia. According to an exemplary embodiment of the present invention, when zirconia powder is added to the liner, the binding force between the liner and zirconia may be increased.

A common commercial liner melts at about 1050° C., but as described above, the melting point of zirconia is about 2715° C., and thus, when the liner containing zirconia powder is fired, the melting point of the liner containing zirconia powder becomes about 1500° C. However, feldspar porcelain has a property of melting when the temperature is above 1000° C. Therefore, in order to bond the fired liner and feldspar porcelain, the melting point of the liner containing zirconia powder should be lowered. According to an exemplary embodiment of the present invention, in order to lower the firing temperature of the liner to 1000° C. or lower, cryolite may be included together as a liner component.

The chemical formula of cryolite is $Na_3AlF_6$. Cryolite forms mainly a bulk or particulate aggregate, and hardly appears as a crystal form. Cryolite does not split, but has parting in three directions, so that it is broken in a cube-like shape. The hardness of cryolite is 2.5 and the specific gravity thereof is 2.97. Cryolite is snow-white and somewhat transparent, but is sometimes reddish brown. Cryolite has glass gloss, and the streak color of cryolite is white. Cryolite is dissolved in sulfuric acid and produces hydrogen fluoride. The melting point of cryolite is about 1020° C. Therefore, cryolite included in the liner components according to an exemplary embodiment of the present invention may serve to lower the firing temperature of the liner to which zirconia powder is added without affecting the color tone or the strength. In this case, the melting point including cryolite may be 900° C. to 1000° C.

Therefore, in the method of manufacturing a dental liner, cryolite is mixed with silicon dioxide, aluminum oxide, and zirconia powder.

1,4-Butanediol for retaining moisture of the dental liner and preventing occurrent of layers is added and mixed (S220).

Generally, a liner in which water and glycerin are mixed shows a phenomenon in which a layer occurs or the liner dries after a certain period of time passes. When the liner is reused after a layer occurs or the liner dries, mixing is needed.

According to an exemplary embodiment of the present invention, the liner including 1,4-butanediol does not dry and does not cause a layer to occur even after a certain period of time. Therefore, since 1,4-butanediol serves to make the liner in a state of being easily coated on zirconia, 1,4-butanediol may be added to the liner components in which silicon dioxide, aluminum oxide, zirconia powder, and cryolite are mixed, and mixing is performed.

Bismuth oxide which imparts fluorescence to zirconia is dissolved in hydrochloric acid or nitric acid. Then, bismuth oxide dissolved in hydrochloric acid or nitric acid is mixed (S230).

Fluorescence is a property possessed by a natural tooth and there is no fluorescent material in a zirconia component. However, a fluorescent material is added to feldspar porcelain. However, the fluorescent material itself which is added to feldspar porcelain has no color and responds only at a certain wavelength, and thus, may not be visually identified.

Feldspar porcelain has higher transparency than various materials used in dentistry. Therefore, feldspar porcelain is veneered on a surface of zirconia so as to be thinner than zirconia. When fluorescence having the same color tone as a natural tooth is imparted to zirconia, feldspar porcelain veneered on an outer surface of zirconia may have different colors depending on the fluorescence of zirconia. Then, feldspar porcelain may be visually identified by the brightening effect.

According to an exemplary embodiment of the present invention, bismuth oxide which imparts fluorescence having the same color tone as a natural tooth to zirconia may be included in the liner components.

Bismuth has an atomic number of 83 and is represented as Bi as an element symbol. Bismuth in an elemental state is a silver-white material which has high density and looks like a shiny metal. Bismuth is also called a deteriorated metal, since it is more brittle than metal and has low thermal and electrical conductivities. On the surface of a pure bismuth sample in the air, a thin bismuth oxide film is slowly formed. This film shows a pink color or rainbow colors composed of various colors.

The kinds of bismuth oxide include bismuth oxide (II), bismuth oxide (III), bismuth oxide (V), and the like, but bismuth oxide generally denotes bismuth oxide (Ill).

A bismuth oxide compound is $Bi_2O_3$. A bismuth oxide is white crystalline powder and is naturally produced as bismuthized $Bi_2O_3.3H_2O$. Bismuth oxide is produced by red-heating bismuth, bismuth hydroxide, bismuth carbonate, bismuth nitrate, and the like in the air or oxygen.

Since bismuth oxide is not decomposed up to 1750° C., it may stand at a high temperature. Therefore, even in the case in which the liner including bismuth oxide is fired at a temperature of 900° C. or higher, bismuth oxide is not decomposed.

Bismuth oxide is soluble in acid, but is insoluble in alkali. Therefore, after bismuth oxide is dissolved in nitric acid or hydrochloric acid, bismuth oxide dissolved in hydrochloric acid or nitric acid is mixed with a mixture to which up to 1,4-butanediol is added.

The method of manufacturing a dental liner for bonding feldspar porcelain and zirconia is a method of making a liner form from powder into a paste. Therefore, when components which have been weighed using an electronic scale are put into a glass vessel and then mixed by a vacuum mixer, the dental liner according to an exemplary embodiment of the present invention may be mixed.

In the method of manufacturing a dental liner, the dental liner may be composed of 50 to 60 parts by weight of silicon dioxide, 5 to 10 parts by weight of aluminum oxide, 10 to 20 parts by weight of zirconia powder, 5 to 10 parts by weight of cryolite, 20 to 30 parts by weight of 1,4-butanediol, 1 to 5 parts by weight of bismuth oxide, and 1 to 5 parts by weight of hydrochloric acid or nitric acid, so that the constituent components included in the liner are evenly mixed.

The thus-manufactured liner is coated on a surface of zirconia. The zirconia coated with the liner is subjected to firing. Here, the firing temperature/retention time may be 1050° C./10 minutes. Only the liner melts at the temperature described above. A porcelain slurry is coated on the melted liner, and zirconia including the porcelain slurry and the liner may be subjected to firing. Here, the firing temperature/retention time may be 900° C./1 minute. Only the liner melts at the temperature described above, and the surface of zirconia is veneered with feldspar porcelain by the melted liner. Firing may be performed in a porcelain furnace.

Hereinafter, the effects of the present invention described above will be described by the experimental examples.

Shear Bond Strength Experiment

Experimental liners including 0, 3, 6, and 9 wt % of zirconia powder were coated on a surface of zirconia, and the case in which the surface of zirconia coated with the experimental liner was veneered with feldspar porcelain refers to Examples 1 to 4 (EL0, EL3, EL6, and EL9), respectively.

The case in which the surface of zirconia which was not coated with a liner was veneered with feldspar porcelain refers to Comparative Example 1 (NL).

The case in which a commercially available liner including silicon dioxide and boron is coated on the surface of zirconia and the surface of zirconia coated with the commercial liner was veneered with feldspar porcelain refers to Comparative Example 2 (CL).

The following Table 1 shows shear bond strength (SBS) values, Weibull distribution values, and fracture aspects for Comparative Examples 1 and 2, and Examples 1 to 4.

TABLE 1

| Classification | Shear bond strength Mean ± SD in MPa | Weibull distribution value | | | Fracture aspect | | |
|---|---|---|---|---|---|---|---|
| | | m | $\sigma 0$ (MPa) | $\sigma 0.05$ (MPa) | $\sigma 00.1$ (MPa) | | |
| | | | | | Adhesive | Cohesive | Mixed |
| NL | 23.6 ± 3.5a | 7.6 | 25.1 | 17.0 | 13.7 | 0 | 0 | 15 |
| CL | 23.0 ± 5.2a | 4.7 | 25.2 | 13.4 | 9.5 | 3 | 0 | 12 |
| EL0 | 25.2 ± 3.8a | 7.4 | 26.8 | 17.9 | 14.4 | 0 | 0 | 15 |
| EL3 | 34.2 ± 4.3b | 8.9 | 36.1 | 25.9 | 21.5 | 0 | 0 | 15 |
| EL6 | 24.1 ± 4.5a | 5.9 | 25.9 | 15.7 | 11.9 | 1 | 0 | 14 |
| EL9 | 22.2 ± 3.7a | 6.2 | 23.2 | 14.4 | 11.0 | 0 | 0 | 15 |

Referring to Table 1, the shear bonding strength value is a mean value (mean)±a standard deviation (SD) value.

The Weibull distribution function is a distribution function which was suggested in 1939 by Swedish physicist W. Weibull for describing a breaking strength of a material and is represented by a cumulative distribution function and a probability density function. A Weibull modulus and a characteristic strength represent the structural reliability of dental ceramic more accurately.

A Weibull modulus m is measure of a defect distribution for brittle materials and determines a shape of a fracture probability distribution curve depending on stress. When the m value is large, the probability that fracture occurs in a material is decreased, and when the m value is small, the probability that fracture occurs in the material even at a low stress is increased. That is, a large m value represents low variability and high reliability.

A characteristic strength $\sigma 0$ represents a strength at which a material may be broken with a probability of 63.21%.

$\sigma 0.05$ and $\sigma 0.01$ represent strengths at which a material may be broken with probabilities of 5% and 1%, respectively.

In the fracture aspect, "Adhesive" refers to fracture in an interface, "Cohesive" refers to internal fracture, and "Mixed" refers to fracture in which both adhesive and cohesive occur.

According to Table 1, the bonding strength value of Example 2 was the highest.

Upon comparison of the Weibull modulus (m), the m value of Comparative Example 2 in which a surface of zirconia was coated with a commercial liner, and then veneered with feldspar porcelain, was 4.7, which was lower than the m value of Comparative Example 1 in which a surface of zirconia which was not coated with a liner was veneered with feldspar porcelain, which was 7.6. The difference between the m value of Example 1 and the m value of Comparative Example 1 was small, and the m values of Examples 3 and 4 were smaller than the m value of Comparative Example 1. However, the m value of Example 2 was 8.9, which was the highest. Therefore, it was confirmed that when a surface of zirconia was coated with an experimental liner including 3 wt % of zirconia powder and then veneered with feldspar porcelain, the fracture probability of zirconia was the lowest.

Considering the fracture aspect of Comparative Example 2, the fracture in the interface occurred in 3 specimens of 15 specimens. In the fracture aspects of the experimental examples except Comparative Example 2 and Example 3, both fracture in the interface and internal fracture occur in all 15 specimens.

FIG. 3 illustrates a scanning electron microscope (SEM) image (left side of the drawing) and a cross-sectional shape of the zirconia/feldspar porcelain interface (right side of the drawing) according to an exemplary embodiment of the present invention.

Figure 3A:
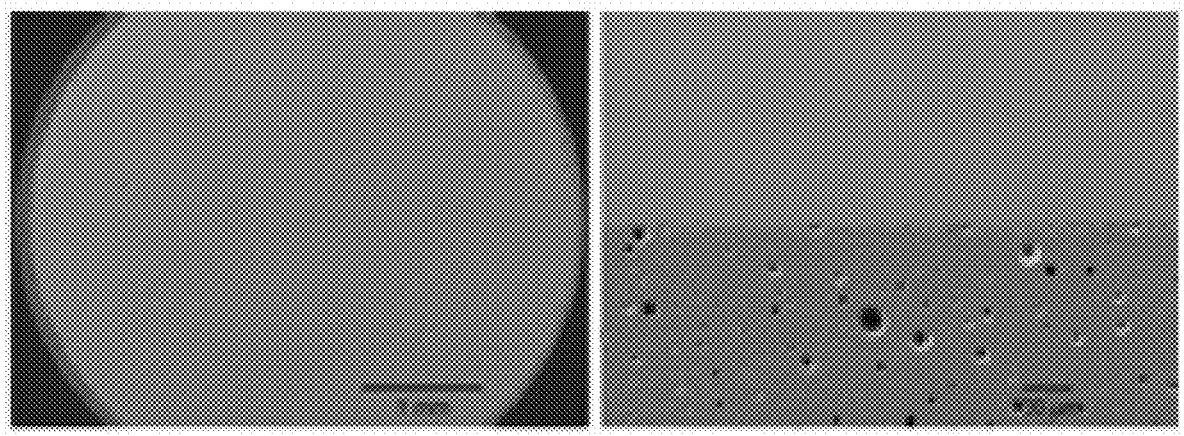
FIGS. 3A to 3C illustrate a scanning electron microscope image according to an exemplary embodiment of the present invention and a cross-sectional shape of a zirconia/feldspar porcelain interface.
Figure 3B:
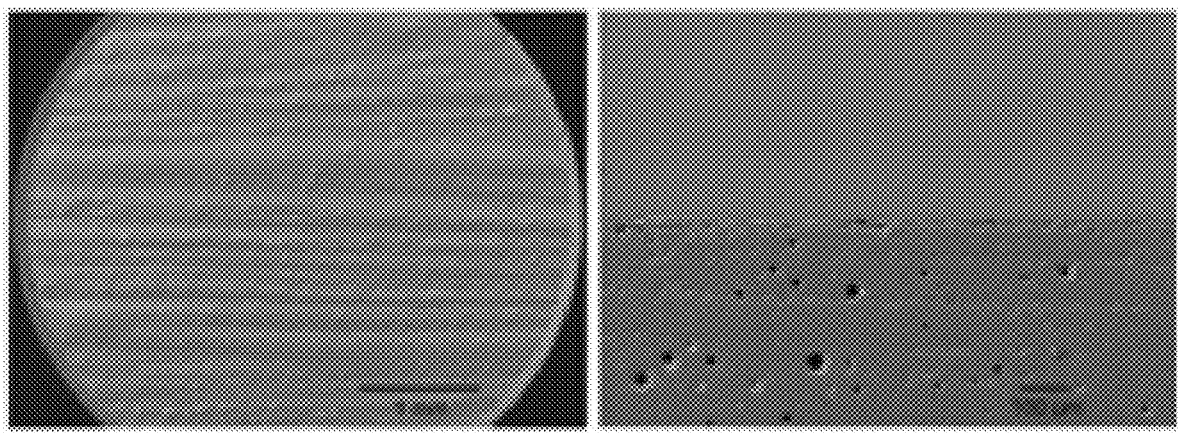
Figure 3C:
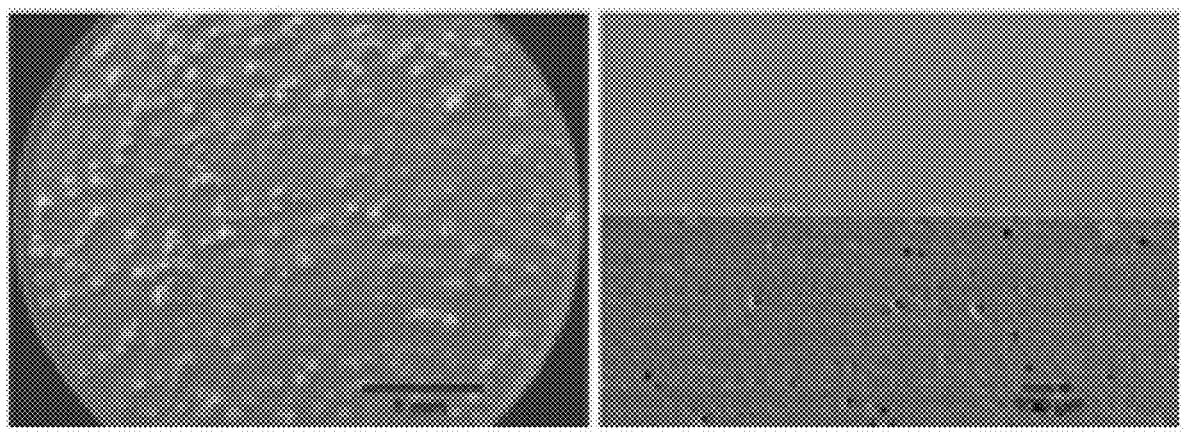

FIG. 3A illustrates an SEM image of a zirconia sample surface and a cross-sectional shape of a zirconia/feldspar porcelain interface with respect to Comparative Example 1 (NL), FIG. 3B illustrates them with respect to Comparative Example 2 (CL), and FIG. 3C illustrates them with respect to Example 2 (EL3).

Referring to FIG. 3, the liner is distributed more evenly on the surface of zirconia of Example 2 than on the surface of zirconia of Comparative Example 2. In addition, upon comparison with Comparative Examples 1 and 2, it was confirmed that Example 2 had the fewest bubbles and the fewest fracture lines.

Three-Point Flexural Strength Experiment

The following Table 2 shows three-point flexural strength (TPFS) values, Weibull distribution values, and fracture aspects for Comparative Example 1 (NL), Comparative Example 2 (CL), and Example 2 (EL3).

TABLE 2

| Classification | Flexural strength Mean ± SD in MPa | Weibull distribution value | | | | Fracture aspect | | | |
|---|---|---|---|---|---|---|---|---|---|
| | | m | σ0 (MPa) | σ0.05 (MPa) | σ00.1 (MPa) | A | B | C | D |
| NL | 57.2 ± 9.3a | 6.0 | 61.6 | 37.5 | 28.6 | 0 | 15 | 0 | 0 |
| CL | 52.4 ± 17.6b | 2.7 | 60.0 | 20.0 | 10.9 | 0 | 14 | 1 | 0 |
| EL3 | 91.9 ± 14.0b | 7.3 | 97.9 | 65.2 | 52.1 | 0 | 9 | 0 | 6 |

Flexural strength refers to a maximum strength which occurs from a specimen when the specimen is pressed at a constant speed. The three-point flexural strength experiment according to the present example is to evaluate the strength of a feldspar porcelain/zirconia double layer system. Feldspar porcelain has weak resistance to tensile stress as compared with compressive stress. Tensile strength refers to resistance occurring in a material for being equal to external force by receiving external force, and when the tensile stress of feldspar porcelain is maximum in the three-point flexural strength experiment, feldspar porcelain may be easily fractured. In addition, when a load is applied, cracks may occur in feldspar porcelain by voids or flaws present in a feldspar porcelain/zirconia interface.

Referring to Table 2, the flexural strength value is a mean value (mean)±a standard deviation (SD) value.

In the Weibull distribution value, a Weibull modulus m represents a shape parameter, a characteristic strength σ0 represents a scale parameter, and each of σ0.05 and σ0.01 represents a strength at which a material may be broken with probabilities of 5% and 1%, respectively.

In the fracture aspect, A represents chipping, B represents cracking, C represents delamination, and D represents catastrophic. Chipping which looks like a bowl being chipped refers to a state in which feldspar porcelain is dented little by little. Cracking refers to a state in which cracks occur in feldspar porcelain. Delamination refers to a state in which feldspar porcelain is separated from zirconia. Catastrophic refers to a state in which feldspar porcelain and zirconia fractures together.

According to Table 2, the flexural strength value of Example 2 was about 1.6 times larger than the flexural strength values of Comparative Examples 1 and 2. However, a difference in the flexural strength values between Comparative Example 1 and Comparative Example 2 was small.

Upon comparison of the Weibull modulus (m), the m value of Comparative Example 2 in which a surface of zirconia coated with a commercial liner was veneered with feldspar porcelain, was 2.7, which was lower than the m value of Comparative Example 1 in which a surface of zirconia which was not coated with a liner was veneered with feldspar porcelain, which was 6. However, the m value of Example 2 was 7.2, which was the highest. Therefore, it was confirmed that when a surface of zirconia coated with an experimental liner including 3 wt % of zirconia powder was veneered with feldspar porcelain, the fracture probability was the lowest.

Upon comparison of the fracture aspect, in Comparative Example 1, cracking occurred in all of 15 specimens. In Comparative Example 2, delamination occurred only in one specimen, and cracking occurred in the remaining 14 specimens. In Example 2, cracking occurred in 9 specimens and catastrophic occurred in 6 specimens, of 15 specimens.

FIG. 4 is strength-displacement graphs represented during a three-point bending strength experiment according to an exemplary embodiment of the present invention and fracture conditions represented in each specimen.

Figure 4A:
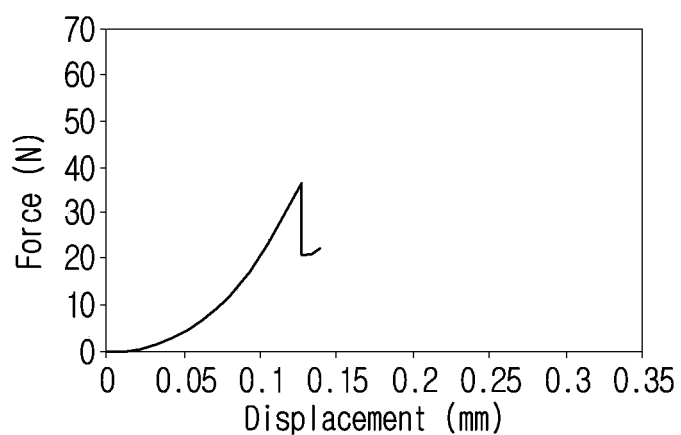
FIGS. 4A to 4C are strength-displacement graphs represented during a three-point bending strength experiment according to an exemplary embodiment of the present invention and fracture conditions represented in each specimen.
Figure 4A:
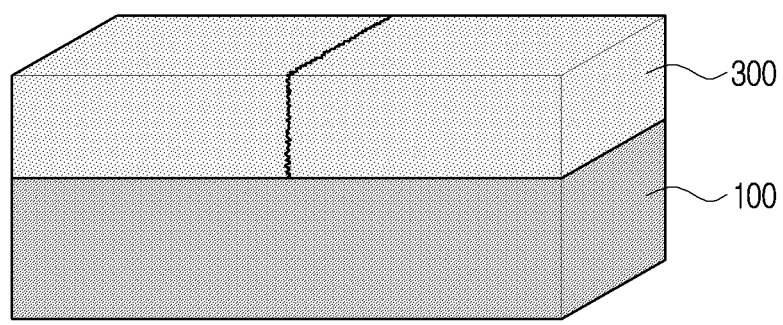
Figure 4B:
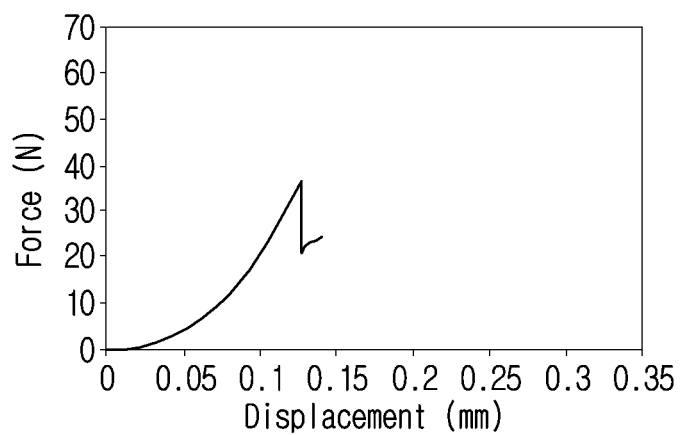
Figure 4B:
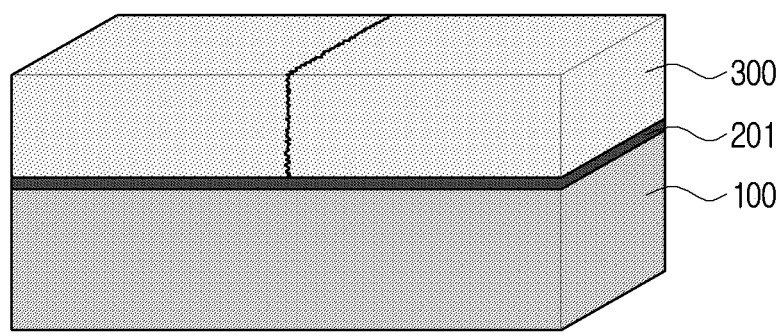
Figure 4C:
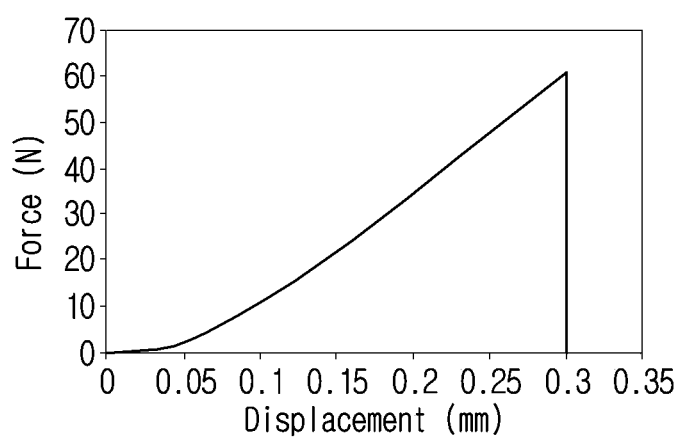
Figure 4C:
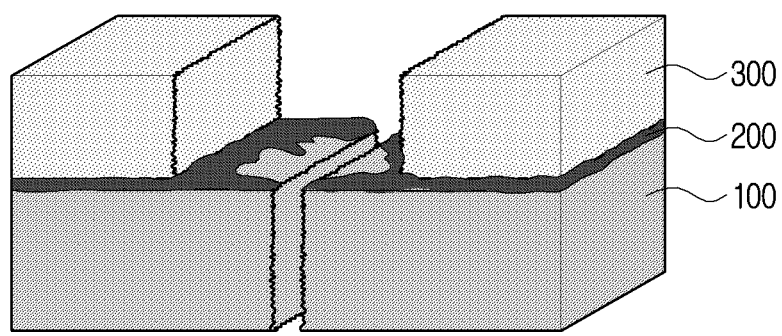

FIG. 4A illustrates a strength-displacement graph shown during an experiment of three-point flexural strength for Comparative Example 1 (NL) and a result of cracking occurrence in feldspar porcelain 300, FIG. 4B illustrates a strength-displacement graph shown during an experiment of three-point flexural strength for Comparative Example 2 (CL) and a result of cracking occurrence in feldspar porcelain 300, and FIG. 4C illustrates a strength-displacement graph shown during an experiment of three-point flexural strength for Example 2 (EL3) and a result of cracking occurrence in feldspar porcelain 300. The catastrophic occurring in FIG. 4C refers to a state in which feldspar porcelain 300 and zirconia 100 coated with the liner 200 were fractured together.

Referring to FIG. 4 and Table 2, in Comparative Example 1, cracking occurred only in feldspar porcelain 300 during the three-point flexural strength experiment, and the fracture aspect did not appear in zirconia 100.

In Comparative Example 2 also, cracking occurred only in feldspar porcelain 300 during the three-point flexural strength experiment, and the fracture aspect did not appear in zirconia 100 coated with a commercial liner 201.

Therefore, the results of the three-point flexural strength experiment for Comparative Examples 1 and 2 show that the binding force between zirconia 100 and feldspar porcelain 300 is low.

The results of the three-point flexural strength experiment for Example 2 show that catastrophic occurred without a sign of chipping, cracking, or delamination. The catastrophic is a phenomenon occurring when the binding force of a material is high, and the results of the three-point flexural strength experiment for Example 2 show that zirconia 100 and feldspar porcelain 300 are firmly bonded by the liner 200.

Although the preferred embodiments of the present invention have been disclosed for illustrative purposes, the present invention is not limited to the specific exemplary embodiments described above, various modifications are possible by those skilled in the art, without departing from the scope and spirit of the invention as disclosed in the accompanying claims, of course, and such modifications should not be understood separately from the technical idea or prospect of the present invention.

The invention claimed is:
1. A dental liner for bonding feldspar porcelain and zirconia, the dental liner comprising:
   silicon dioxide;
   aluminum oxide;
   1,4-butanediol for retaining moisture of the dental liner and preventing occurrence of layers; and zirconia powder for reinforcing chemical bonding between the dental liner and the zirconia to bond the dental liner and the zirconia.

2. The dental liner as claimed in claim 1, further comprising: cryolite for melting the dental liner at a temperature in a predetermined range, when the dental liner is bonded to the zirconia and then fired.

3. The dental liner as claimed in claim 2, wherein the temperature in a predetermined range is 900° C. to 1000° C.

4. The dental liner as claimed in claim 1, further comprising: bismuth oxide for imparting fluorescence to the zirconia,
wherein the bismuth oxide is dissolved in hydrochloric acid or nitric acid.

5. A method of manufacturing a dental liner for bonding feldspar porcelain and zirconia, the method comprising:
mixing silicon dioxide, aluminum oxide, zirconia powder, and cryolite;
adding 1,4-butanediol for retaining moisture of the dental liner and preventing occurrence of layers and performing mixing; and
dissolving bismuth oxide for imparting fluorescence to the zirconia in hydrochloric acid or nitric acid and mixing the bismuth oxide dissolved in hydrochloric acid or nitric acid.

6. The method of manufacturing a dental liner as claimed in claim 5, wherein the dental liner includes:
50 to 60 parts by weight of the silicon dioxide;
5 to 10 parts by weight of the aluminum oxide;
10 to 20 parts by weight of the zirconia powder;
5 to 10 parts by weight of the cryolite;
20 to 30 parts by weight of the 1,4-butanediol;
1 to 5 parts by weight of the bismuth oxide; and
1 to 5 parts by weight of the hydrochloric acid or nitric acid.

* * * * *